Figure 1:
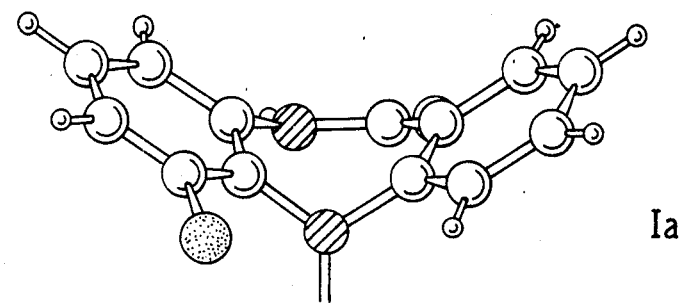
Figure 1:
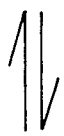
Figure 1:
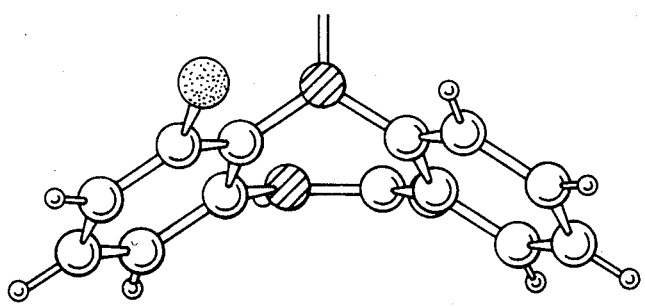
Figure 1:
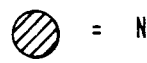
Figure 1:
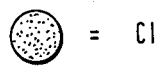
Figure 1:
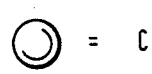
Figure 1:
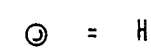

United States Patent [19]

Trummlitz et al.

[11] Patent Number: 4,668,674

[45] Date of Patent: May 26, 1987

[54] (+)-6-CHLORO-5,10-DIHYDRO-5-[(1-METH-YL-4-PIPERIDINYL)-ACETYL]-11H-DIBEN-ZO[B,E][1,4]DIAZEPIN-11-ONE, THE ISOLATION THEREOF AND ITS USE AS A PHARMACEUTICAL MATERIAL

[75] Inventors: Günter Trummlitz, Warthausen; Wolfhard Engel, Biberach; Wolfgang Eberlein, Biberach; Gerhard Mihm, Biberach, all of Fed. Rep. of Germany; Antonio Giachetti, Mailand, Italy

[73] Assignee: Dr. Karl Thomae GmbH, Biberach an der Riss, Fed. Rep. of Germany

[21] Appl. No.: 898,153

[22] Filed: Aug. 19, 1986

[30] Foreign Application Priority Data

Sep. 5, 1985 [DE] Fed. Rep. of Germany ....... 3531682

[51] Int. Cl.$^4$ .................... C07D 243/38; A61K 31/55

[52] U.S. Cl. .................... 514/220; 540/522
[58] Field of Search .................... 540/522; 514/220

[56] References Cited

U.S. PATENT DOCUMENTS 4,567,178 1/1986 Eberlein et al. .................... 540/522

Primary Examiner—Robert T. Bond
Attorney, Agent, or Firm—David E. Frankhouser; Alan R. Stempel

[57] ABSTRACT

There are described (+)-6-chloro-5,10-dihydro-5-[(1-methyl-4-piperidinyl)-acetyl]-11H-dibenzo [b,e][1,4-]diazepin-11-one, the isolation thereof from a mixture of enantiomers and its use as a pharmaceutical material.

The compound is characterized by a powerful activity against ulcers of the gastro-intestinal tract.

5 Claims, 1 Drawing Figure

U.S. Patent    May 26, 1987    4,668,674

Ia

Ib

= N

= Cl

= C

= H

(+)-6-CHLORO-5,10-DIHYDRO-5-[(1-METHYL-4-PIPERIDINYL)-ACETYL]-11H-DIBENZO[B,E][1,4]DIAZEPIN-11-ONE, THE ISOLATION THEREOF AND ITS USE AS A PHARMACEUTICAL MATERIAL

The invention relates to (+)-6-chloro-5,10-dihydro-5-[(1-methyl-4-piperidinyl)acetyl]-11H-dibenzo[b,e][1,4]-diazepin-11-one, the isolation thereof from a mixture of enantiomers and its use as a pharmaceutical material.

European Patent Application No. 83 100 677.0 (Publication No. 0 085 892) describes substituted dibenzodiazepinones, processes for preparing them and pharmaceutical compositions containing them. It also describes, inter alia, the compound 6-chloro-5,10-dihydro-5-[(1-methyl-4-piperidinyl)-acetyl]-11H-dibenzo[b,e][1,4]diazepin-11-one of formula I:

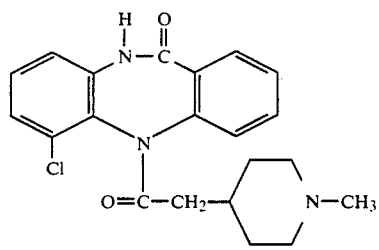

(I)

It has now been found that, surprisingly, the compound of formula I occurs in enantiomeric forms which are stable at ambient temperature and that the mixture of enantiomers can be resolved. This type of behaviour was unpredictable for the following reasons:

A study of formula I shows no asymmetrical atoms. However, it is known that in compounds of this kind the seven-membered ring is not planar but boat-shaped and thus the tricyclic compounds of the formula I type can theoretically occur in two mirror-symmetrical chiral configurations. However, both forms are in equilibrium and should not be capable of separation. Thus, the substance pirenzepine of formula II

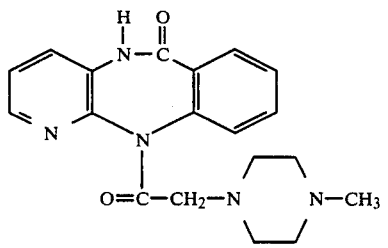

(II)

has been shown to occur in two enantiomeric forms which rapidly interconvert (cf. Arzneim.-Forsch./Drug Res. 34(II), 8, 849–859 (1984)). The transformation from one form into the other, however, takes place so rapidly even at ambient temperature that it is impossible to carry out a separation into the individual forms. It was therefore assumed that the compound of formula I would behave similarly.

It has now surprisingly been found that the compound of formula I can be resolved into the optical enantiomers thereof and, even more surprisingly, that the optical enantiomers do not racemise even at temperatures of up to 150° C. These facts make it possible to use only one enantiomer, in this case the physiologically highly effective (+) form, in the therapy of diseases of the gastrointestinal tract.

The two possible enantiomeric configurations of the tricyclic ring system of the compound of formula I are shown in FIG. 1.

It has been found that the enantiomer with the specific optical rotation of $[\alpha]_D^{20} = +165.9°$ (C=0.71; in chloroform) is the biologically effective form and, in its tricyclic molecular part, it has the configuration Ia, as demonstrated by X-ray structural analysis. For this analysis, salt crystals were prepared with L-tartaric acid and the enantiomers of formula I and then investigated by x-ray analysis; evaluation of the results yielded the configuration Ia.

A racemate obtained by the methods mentioned in European Patent No. 83 100 677.0 referred to hereinbefore can be resolved into the optically active enantiomers by methods known per se, for example using an optically active acid. Examples of optically active acids include, in particular, L-(+) or D-(−) tartaric acid, one of the derivatives thereof such as (+) or (−) diacetyltartaric acid, (+) or (−) monomethyltartrate or (+) camphoric acid. Preferably, L-(+) or D-(−) tartaric acid is used for the resolution. The mixture of enantiomers of formula I is reacted with one of the above-mentioned optically active acids in equimolar quantities in a solvent and the crystalline diastereomeric salts obtained are separated, using their different solubilities. This reaction may be carried out in any type of solvent provided it demonstrates sufficiently different solubilities for the salts. Preferably, methanol, ethanol or mixtures thereof in a ratio by volume of 50:50, for example, are used. By adding alkali to the salts, the enantiomeric bases can be liberated.

The (+)-6-chloro-5,10-dihydro-5-[(1-methyl-4-piperidinyl)-acetyl]-11H-dibenzo[b,e][1,4]diazepin-11-one thus obtained, unlike the (−) form, has a Powerful anti-ulcerative effect and an inhibitory effect on the secretion of gastric acid and also demonstrates a favourable effect on various other diseases of the gastro-intestinal tract, of which low bowel distress symptoms should be particularly emphasised. It has been found that in order to achieve the same results with the (+) form, approximately only half the dosage which would be needed when using the mixture of enantiomers need be administered; on the other hand, at least 50 times the quantity would be required when using the (−) form in order to achieve the same results.

The protective effect on the stomach conferred by the two enantiomers of formula I was investigated using a model experiment; the method and results are described hereinafter.

Effect on rats after ligature of the pylorus

Method:

Male Wistar rats (weighing between 100 and 125 g) which had fasted for 24 hours but had free access to water was used. The rats were divided up into groups of 10 animals. The rats were anaesthetised with ether and the abdominal cavity was opened up by longitudinal cutting and the pylorus was tied off. Before ligature of the pylorus, the substances dissolved in saline solution were administered intravenously in metered doses (0.1 ml/100 g of body weight), the intravenous administration was carried out immediately before ligature of the pylorus; control animals were given only the saline solution. Two hours after the ligature the animals were killed and the stomachs were carefully removed. The stomach contents were collected and centrifuged for 15 minutes at 4000 rpm, then the supernatant was separated off in order to determine the volume of gastric juices. Using a pH measuring apparatus (I.T.T. Radiometer PHM 62) the acidity was measured by titration to pH 7 of 1 ml samples of the gastric juices.

The total acid was calculated from the product of the measured volume and acidity (microequivalent.ml) and expressed as microequivalents over 2 or 4 hours. The data obtained from the individual pretreated rats were compared with the average values obtained from the control groups and expressed as the percentage deviation. The percentage values were transformed into probits and subjected to linear regression analysis in order to determine the $ED_{50}$ values for volume and total acid secretion, whilst observing 95% confidence limits.

| Results: | |
|---|---|
| Substance | $ED_{50}$ value mg/kg rat i.v. |
| (+) form | 0.18 |
| (−) form | >>3* |

*At 3 mg/kg there is only a 1.6% deviation from the average values of untreated control groups.

The experiment clearly shows that the (+) form is the form which carries the activity.

The dextrorotatory enantiomer of formula I may also occur in the form of other physiologically acceptable salts, after reaction with inorganic or organic acids. Suitable acids include, for example, hydrochloric, hydrobromic, sulphuric, (−) tartaric, fumaric and citric acid.

The invention further relates to pharmaceutical compositions which contain the dextrorotatory enantiomer of formula I. The (+) form can be incorporated, in known manner, in the conventional pharmaceutical preparations, e.g. in solutions, suppositories, tablets, coated tablets, capsules or infusions. The daily dosage is generally between 0.001 and 0.5, preferably between 0.002 and 0.25, more particularly between 0.005 and 0.1, mg/kg of body weight, possibly administered in the form of several, preferably 1 to 3, individual doses, in order to achieve the desired effect.

The following Examples serve to illustrate the invention

EXAMPLE 1

(+)-6-Chloro-5,10-dihydro-5-[(1-methyl-4-piperidinyl)-acetyl]-11H-dibenzo[b,e][1,4]diazepin-11-one-L-(+)-tartrate 25 g of L-(+)-tartaric acid ("natural" tartaric acid) are dissolved in 100 ml of ethanol and added to a boiling solution of 127.9 g of (±)-6-chloro-5,10-dihydro-5-[(1-methyl-4-piperidinyl)-acetyl]-11H-dibenzo[b,e][1,4-]diazepin-11-one in 900 ml of ethanol.

On cooling, 68.5 g of 6-chloro-5,10-dihydro-5-[(1-methyl-4-piperidinyl)-acetyl]-11H-dibenzo[b,e][1,4-]diazepin-11-one-L-(+)-tartrate crystallise out of this solution. This is a 90:10 concentration of the (+) form. The mother liquor is used to isolate the (−) form (see below). 50 g of the above mentioned tartrate (concentrated (+) form) are stirred into 100 ml of water, 200 ml of methylene chloride are added and, with stirring, solid potassium carbonate is added until the aqueous phase is precipitated on the bottom of the flask. The aqueous phase separated off is extracted twice more with methylene chloride. The combined organic phases are dried over magnesium sulphate and then concentrated by evaporation in vacuo. The residue (44.1 g) is reacted sith 8.6 g of L-(+) tartaric acid in 500 ml of hot ethanol. On cooling, 42.1 g of (+)-6-chloro-5,10-dihydro-5-[(1-methyl-4-piperidinyl)-acetyl]-11H-dibenzo[b,e][1,4-]diazepin-11-one-L-(+)-tart rate crystallise out.

By working up the mother liquors, particularly after separation of the concentrated (−) form by crystallisation with D-(−) tartaric acid, it is possible to isolate a further 28.25 g of the (+) form.

The yield of pure (+)-6-chloro-5,10-dihydro-5-[(1-methyl-4-piperidinyl)-acetyl]-11H-dibenzo[b,e][1,4-]diazepin-11-one-L-(+)-tartrate, based on racemic 6-chloro-5,10-dihydro-5-[(1-methyl-4-piperidinyl)-acetyl]-11H-dibenzo[b,e][1,4]diazepin-11-one, is thus 85% of theory.

Melting Point: 175° C. (decomposition)
$C_{21}H_{22}ClN_3O_2 \times \frac{3}{4}C_4H_6O_6$ (496.45):
Calculated: C 58.07; H 5.38; Cl 7.14; N 8.46;
Found: 57.88; H 5.60; Cl 6.88; N 8.32

EXAMPLE 2

(+)-6-Chloro-5,10-dihydro-5-[(1-methyl-4-piperidinyl)-acetyl]-11H-dibenzo[b,e][1,4]diazepin-11-one 5 g of (+)-6-Chloro-5,10-dihydro-5-[(1-methyl-4-piperidinyl)-acetyl]-11H-dibenzo[b,e][1,4]diazepin-11-one-L-(+)-tart rate were dissolved in water, mixed with potash and extracted with methylene chloride. The extracts were combined and evaporated off several times with ethanol. 3.9 g (95% of theory) of (+)-6-chloro-5,10-dihydro-5-[(1-methyl-4-piperidinyl)-acetyl]-11H-dibenzo[b,e][1,4]diazepin-11-one were obtained.

Melting point: 112° C.; $[\alpha]_D^{20} = +165.9°$ (c=0.71; $CHCl_3$).

The optical purity of the product thus obtained (all others were similarly characterised) was checked by chiral HPLC, as well as the constancy of optical rotation on further recrystallisation. A column of (R)-N-3,5-dinitrobenzoyl-leucine on 5 micron aminopropyl silica [J.T. Baker Chemical Co.: Bakerbond 250×4.6 mm], a column with Rheodym inlet valve no. 7125 with a 250 microlitre sample loop (Spectra Physics Integrator System I) together with a Perkin Elmer Liquid Chromatograph (Series IIIB), Spectrophotometer LC 75 and Scheiber Type 561 was used; n-hexane/ ethanol/methanol (200:8:8) was used as the mobile phase.

In this way it was possible to demonstrate that the content of (+) form is over 98% and the other enantiomer is present in a quantity of less than 2%.

EXAMPLE 3

(−)-6-Chloro-5,10-dihydro-5-[(1-methyl-4-piperidinyl)-acetyl]-11H-dibenzo[b,e][1,4]diazePin-11-one-D-(-)-tart rate Reaction of the mixture of enantiomers with D-(−) tartaric acid, analogously to Example 1, yields the (−) enantiomer in the form of the D-(−) tartrate.

Melting Point: 175° C. (decomposition).
$C_{21}H_{22}ClN_3O_2 \times \frac{3}{4}C_4H_6O_6$ (496.45): Calculated: C 58.07; H 5.38; Cl 7.14; N 8.46; Found: 57.82; H5.49; Cl 6.90; N 8.25

EXAMPLE 4

(−)-6-Chloro-5,10-dihydro-5-[(1)methyl-4-piperidinyl)-acetyl]-11H-dibenzo[b,e][1,4]diazeoin-11-one The base was liberated from (−)-6-chloro-5,10-dihydro-5-[(1-methyl-4-piperidinyl)-acetyl]-11H-dibenzo[b,e][1,4]- diazepin-11-one-D-(−)-tartrate analogously to Example 2.

Melting point: 112° C.; $[\alpha]_D^{20} = -165.6°$ (c=0.79; chloroform).

EXAMPLE 5

(−)-6-Chloro-5,10-dihydro-5-[(1-methyl-4-piperidinyl)-acetyl]11H-dibenzo[b,e][1,4]diazepin-11-one-D-(−)-tartrate (−)6-Chloro-5,10-dihydro-5-[(1-methyl-4-piperidinyl)-acetyl]-11H-dibenzo[b,e][1,4]diazepin-11-one-D-(−)-tartrate can be obtained in an 82% yield from the mother liquor of Example 1, which contains the (−) enantiomer in an approximately 75:25 concentrated molar ratio, by liberating with aqueous potash solution and recrystallising twice, with the addition of D-(−)tartaric acid, from hot ethanol.

Melting point: 175° C. (decompostion)
$C_{21}H_{22}ClN_3O_2$ x $\frac{3}{4}C_4H_6O_6$ (496.45); Calculated: C 58.07; H 5.38; Cl 7.14; N 8.46; Found: 58.02; H 5.19; Cl 7.02; N 8.32

EXAMPLE 6

(+)-6-Chloro-5,10-dihydro-5-[(1-methyl-4-piperidinyl)-acetyl]-11H-dibenzo[b,e][1,4]diazepin-11-one-L-(+)-tartrate (+)-6-Chloro-5,10-dihydro-5-[(1-methyl-4-piperidinyl)-acetyl]-11H-dibenzo [b,e][1,4]diazepin-11-one-L-(+)-tartrate can be obtained in an 86% yield from the mother liquor of Example 3, which contains the (+) enantiomer in an approximately 75:25 concentrated ratio, by liberation and crystallisation in the Presence of L-(+)tartaric acid from hot ethanol.

Melting Point: 175° C. (decompostion)
$C_{21}H_{22}ClN_3O_2$ x $\frac{3}{4}C_4H_6O_6$ (496.45); Calculated: C 58.07; H 5.38; Cl 7.14; N 8.46; Found: C 57.91; H 5.12; Cl 6.80; N 8.09

EXAMPLE 7

Racemisation Test

In different pH ranges (pH 1 to 9), in different solvents (water, glycol) and in the form of its melt,(+)-6-chloro-5,10-dihydro-5-[(1-methyl-4-piperidinyl )-acetyl]-11H-dibenzo[b,e][1,4]diazepin-11-one showed no racemisation of the substance of Example lx at temperatures of up to 150° C. over a period of fifteen minutes. The optical rotation remained constant and HPLC showed that no (−) enantiomer had formed.

The preparation of some pharmaceutical forms will now be illustrated by means of some examples

EXAMPLE I

Tablets containinq 0.5 mg of (+)-6-chloro-5,10-dihydro-5-[(1-methyl-4-piperidinyl)-acetyl]-11H-dibenzo[b,e][1,4]diazepin-11-one Composition:

| One tablet contains: | |
| --- | --- |
| Active substance | 0.5 mg |
| Lactose | 152.5 mg |
| Potato Starch | 65.0 mg |
| Magnesium stearate | 2.0 mg |
| | 220.0 mg |

Method of preparation:

A 10% mucilage is prepared from potato starch by heating. The active substance, lactose and remaining potato starch are mixed together and granulated with the mucilage through a screen with a 1.5 mm mesh size. The granulate is dried at 45° C., passed through the same screen again, mixed with magnesium stearate and compressed to form tablets.

Weight of tablet: 220 mg
Punch: 9 mm

EXAMPLE II

Coated tablets containing 0.5 mg of (+)-6-chloro-5,10-dihydro-5-[(1-methyl-4-piperidinyl)acetyl]-11H-dibenzo[b,e][1.4]diazepin-11-one The tablets prepared in Example I are coated in known manner with a coating consisting essentially of sugar and talc. The finished coated tablets are polished with beeswax.

Weight of coated tablet: 300 mg

EXAMPLE III

Ampoules containing 0.2 mg of (+)-6-chloro-5,10-dihydro-5-[(1-methyl-4-piperidinyl)-acetyl]-11H-dibenzo[b,e][1,4]diazepin-11-one hydrochloride Composition:

| 1 ampoule contains: | |
| --- | --- |
| Active substance | 0.2 mg |
| Sodium chloride | 8.0 mg |
| Distilled water ad | 1 ml |

Method of preparation:

The active substance and sodium chloride are dissolved in distilled water and then made up to the volume specified. The solution is filtered sterile and transferred into 1 ml ampoules.

Sterilisation: 20 minutes at 120° C.

EXAMPLE IV

Suppositories containing 1 mg of (+)-6-chloro-5,10-dihydro-5-[(1-methyl-4-piperidinyl)-acetyl]-11H-dibenzo[b,e][1,4]diazepin-11-one Composition:

| 1 suppository contains: | |
| --- | --- |
| Active substance | 1.0 mg |
| Suppository mass (e.g. Witepsol W 45$^R$) | 1699.0 mg |
| | 1700.0 mg |

Method of oreparation:

The finely powdered active substance is suspended in the suppository mass which has been melted and cooled to 40° C. The mass is poured at 37° C. into slightly chilled suppository moulds.

Weight of suppository: 1.7 g

EXAMPLE V

Drops containing
(+)-6-chloro-5,10-dihydro-5-[(1-methyl-4-piperidinyl)-acetyl]-11H-dibenzo[b,e][1,4]diazepin-11-one Composition:

| 100 ml of drops solution contains: | |
|---|---|
| Methyl p-hydroxybenzoate | 0.035 g |
| Propyl p-hydroxybenzoate | 0.015 g |
| Aniseed oil | 0.05 g |
| Menthol | 0.06 g |
| Pure ethanol | 10.0 g |
| Active substance | 0.1 g |
| Sodium cyclamate | 1.0 g |
| Glycerol | 15.0 g |
| Distilled water ad | 100.0 ml |

Method of preparation

The active substance and sodium cyclamate are dissolved in about 70 ml of water and glycerol is added. The p-hydroxybenzoates, aniseed oil and menthol are dissolved in ethanol and this solution is added to the aqueous solution with stirring. Finally, the solution is made up to 100 ml with water and filtered to remove any suspended particles.

What is claimed is:

1. (+)-6-Chloro-5,10-dihydro-5-[(1-methyl-4-piperidinyl-acetyl]-11H-dibenzo[b,e][1,4]diazepin-11-one or a physiologically acceptable salt thereof.

2. A pharmaceutical composition comprising (+)-6-chloro-5,10-dihydro-5-[(1-methyl-4-piperidinyl)-acetyl]-11lH-dibenzo[b,e][1.4]diazepin-6-one or a physioloqically acceptable salt thereof together with a pharmaceutically acceptable carrier.

3. A method for inhibiting gastric acid secretion which comprises administering to a host a gastric acid secretion inhibiting amount of (+)-6-chloro-5,10-dihydro-5[(1-methyl-4-piperidinyl)-acetyl]-11H-dibenzo[b,e][1.4]diazepin-11-one, or a physiologically acceptable salt thereof.

4. A method of treating ulcers of the gastro-intestinal tract which comprises administering to a host in need of such treatment an anti-ulcerative amount of (+)-6-chloro-5,10-dihydro-5[(1-methyl-4-piperidinyl)-acetyl]-11H-dibenzo[b,e][1,4]diazepin-11-one, or a physiologically acceptable salt thereof 5. A Process for preparing (+)-6-chloro-5,10-dihydro-5-[(1-methyl-4-piperidinyl)-acetyl]-11H-dibenzo[b,e][1,4]diazepin-11-one, from the racemate thereof, which comprises converting the racemate into diastereomeric salts using an optically active acid in a solvent, separating these salts using their different solubilities, and obtaining the free base from the resulting salt of the (+) form by the addition of alkali.

* * * * *